United States Patent [19]

McBride

[11] Patent Number: 5,964,997
[45] Date of Patent: Oct. 12, 1999

[54] BALANCED ASYMMETRIC ELECTRONIC PULSE PATTERNS FOR OPERATING ELECTRODE-BASED PUMPS

[75] Inventor: Sterling E. McBride, Lawrenceville, N.J.

[73] Assignee: Sarnoff Corporation, Princeton, N.J.

[21] Appl. No.: 08/821,480

[22] Filed: Mar. 21, 1997

[51] Int. Cl.[6] .................................................. G01N 27/26
[52] U.S. Cl. ...................... 204/451; 204/454; 204/601; 204/450
[58] Field of Search ................................ 204/450, 451, 204/457, 458, 600, 601, 608, 609

[56] References Cited

U.S. PATENT DOCUMENTS

| | | | |
|---|---|---|---|
| 3,923,426 | 12/1975 | Theeuwes | 204/630 |
| 4,101,220 | 7/1978 | Bean et al. | 356/105 |
| 4,316,233 | 2/1982 | Chato et al. | 361/233 |
| 5,015,351 | 5/1991 | Miller | 204/515 |
| 5,178,737 | 1/1993 | Lai | 204/455 |
| 5,194,133 | 3/1993 | Clark et al. | 204/608 |
| 5,292,416 | 3/1994 | Novotny et al. | 204/453 |
| 5,585,069 | 12/1996 | Zannzucchi et al. | 422/100 |

FOREIGN PATENT DOCUMENTS

| | | |
|---|---|---|
| 0 595 290 A2 | 4/1994 | European Pat. Off. . |
| 0 672 835 A1 | 9/1995 | European Pat. Off. . |

OTHER PUBLICATIONS

Fuhr et al., "Microfabricated electrohydrodynamic (EHD) pumps for liquids of higher conductivity," *INSPEC Abstract Number: C9305–3260J–002*, Sep. 1992.

Fuhr et al., "Pumping of water solutions in microfabricated electrohydrodynamic systems," *INSPEC Abstract Number: C9301–3260J–006*, Feb. 1992.

Richter et al., "The electrohydrodynamic micro flow meter," *INSPEC Abstract Number: A9213–4780–013, B9207–7230–074*, Jun. 1991.

Bart et al., Sensors and Actuators, A21–A23: 193–197, 1990 Month unavailable.

Dasgupta et al., Anal. Chem., 66: 1792–1798, 1994 Month unavailable.

Howe et al., IEEE Spectrum, pp. 29–35, Jul. 1990 Month unavailable.

Mehregany, Circuits and Devices, pp. 14–22, 1993 Month unavailable.

Melcher, The Physics of Fluids, 9(8): 1548–1555, 1966 Month unavailable.

Pickard, Journal of Applied Physics, 34(2): 246–250, 1963 Month unavailable.

Richter et al., Sensors and Actuators, A 29: 159–168, 1991 Month unavailable.

Stuetzer, Journal of Applied Physics, 31(1): 136–146, 1960 Month unavailable.

Wenzel et al., Trans. of Electron Devices, 35(6): 735–743, 1988 Month unavailable.

*Primary Examiner*—Robert Warden
*Assistant Examiner*—Alex Noguerola
*Attorney, Agent, or Firm*—William J. Burke

[57] ABSTRACT

Provided is a method of operating an electrode-based pump to pump a liquid, the method comprising periodically reversing the voltage polarity applied to the electrodes of the pump while maintaining a net flow of liquid in a desired direction. Further provided is an apparatus for pumping liquid with an electrode-based pump comprising: a channel of capillary dimensions; a pump comprising at least two electrodes inserted into the channel; a controller for controlling the voltages applied to the electrodes such that the pumps operate under a sequentially repeated pattern of polarity cycles, and such that over the period of the repeated pattern either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_1$ carried by the current associated with the other polarity is between about 1:½ and about ½:1. Additionally provided are apparatuses and methods for electrophoresis.

35 Claims, 1 Drawing Sheet

BALANCED ASYMMETRIC ELECTRONIC PULSE PATTERNS FOR OPERATING ELECTRODE-BASED PUMPS

The present invention is directed to a method of operating an electrode-based pump, which can be an electrohydrodynamic pump, or operating an electrophoresis apparatus, using an asymmetric electrical pulse pattern.

A number of related patents have been granted and applications have been filed on liquid distribution systems that use electrode-based pumps including U.S. Pat. No. 5,585,069, issued Dec. 17 1996; U.S. Pat. No. 5,593,838, issued January 14, 1997; 08/454,771, filed May 31, 1995 (DSRC 11402B), abandoned a continuation of which, 08/789,739, is granted as U.S. Pat. No. 5,863,708, issued Jan. 27, 1997; U.S. Pat. No. 5,643,738, issued Jul. 1, 1997; U.S. Pat. No. 5,681,484 issued Oct. 28, 1997; U.S. Pat. No. 5,755,942, issued May 26, 1998; 08/454,768, filed May 31, 1995, abandoned, a continuation of which is granted as U.S. Pat. No. 5,858,804, issued Jan. 12, 1999; 08/556,036, filed May 31, 1995 which is granted as U.S. Pat. No. 5,846,396, issued Dec. 8, 1990; U.S. Pat. No. 5,632,876, issued May 27 1997; U.S. Pat. No. 5,858,193, issued Ja. 12, 1999; U.S. application Ser. No. 08/645,966, May 10, 1996 (DSRC 11717B); U.S. Pat. No. 5,603,351 issued Feb. 18, 1997; and U.S. application Ser. No. 08/744,386, Nov. 7, 1996 (DSRC 12385A). These patent and applications are hereby incorporated herein by reference in their entirety.

Such systems that are pumped using electrodes acting as pumps that have no moving parts can be used for example to relay liquids in very small devices to conduct multiple parallel but non-equivalent small-scale syntheses or to conduct multiple small-scale analytical reactions. In the course of operating such electrode-based pumping devices, the present applicant observed that some of the liquids desired to be pumped were susceptible to having unwanted electrochemical reactions occur at the pumping electrodes. Where this electrochemistry leads to substantial bubble formation at the pumping electrodes, pumping efficiency is diminished, or even stops.

Accordingly, the invention provides methods for reducing or eliminating such bubbling at electrodes. In addition to improving electrode-based pumping, the invention is applicable in electrophoresis applications, where bubbling can also interfere with process efficiency. The process of the invention utilizes periodic reversals in the polarity applied to electrodes while maintaining a sufficient electronic impetus for pumping or electrophoresis in a desired direction. It is believed that, in the context of slab gel electrophoresis, particularly "submarine" gels that are electrophoresed when submerged under a layer of buffer, so-called "pulsed field" methods have been used that apply modulations in field orientation to orient very large molecules during the electrophoresis process. See Schwartz and Cantor, *Cell* 37:67–75, 1984. These are modulations are not believed to be reversals in voltage polarity applied to two reference electrodes. The range of pulse lengths typically used, 1 second to 90 minutes, corresponds to a frequency range of 1 to about $2 \times 10^{-4}$ Hz. It is not believed that there has been any motivation or suggestion for using such field modulation methods in a capillary environment, and indeed the goal of shifting the field lines between orientations where they obliquely intersect the direction of electrophoresis would be difficult to achieve in a capillary environment. Further, such methods have not been applied so as to minimize or eliminate bubbling.

Complex arrays of electrodes have been applied in "traveling wave" pumping protocols with the intention of pumping liquids of higher conductivity. See, Fuhr et al., *J. Microelectromechanical Systems* 1:141–147, 1992. These methods apply traveling waves of voltage amplitude changes, but do not apply polarity reversals as in the methods of the invention. Further, while the methods of the invention can be applied to complex arrangements of electrodes, they can also, in contrast to traveling wave methods, be applied to very simple two-electrode pumps. Accordingly, pumps of the invention, but not those using complex electrode arrangements, can be readily integrated into high-density microfabricated fluid distributing systems or electrophoresis systems.

By the present invention, methods of operating electrode-based pumps while minimizing bubbling due to electrolysis and other electrochemical reactions have been identified. The method operates by periodically reversing the polarity applied to the electrodes, but doing this in a manner that results in bulk liquid flow (pumping) in the direction desired.

SUMMARY OF THE INVENTION

In a first embodiment, the invention provides a method of operating an electrode-based pump to pump a liquid, the method comprising periodically reversing the voltage polarity applied to the electrodes of the pump while maintaining a net flow of liquid in a desired direction. Preferably, the method further comprises selecting a pattern of polarity reversals and an associated voltage amplitude profile to reduce or eliminate the nucleation of gas at the electrodes. Preferably, the voltage polarity reversals are applied by repeating a defined pattern with a defined frequency, wherein the defined pattern is made up of a voltage amplitude profile of a first polarity, which first polarity causes pumping in the desired direction, and a voltage amplitude profile of a second polarity opposite that of the first. Preferably, the frequency is at least about 10 Hz, more preferably, the frequency is from about 10 Hz to about 100 MHz, yet more preferably from about 100 Hz to about 10 kHz, yet still more preferably from about 100 Hz to about 1 kHz.

Preferably, the maximum voltage applied of the first polarity is greater than the maximum voltage applied of the second polarity. Preferably, the maximum voltage of the first polarity is at least about 10 V, more preferably at least about 100 V, yet more preferably at least about 500 V. Preferably, the maximum voltage of the second polarity is no more than about 50% of the maximum voltage of the first polarity, more preferably no more than about 40%, yet more preferably no more than about 30%. Of course, the particular voltage applied with be related to such factors as the geometry of the pumping electrodes and the associated fluid channel and the susceptibility of the pumped liquid to dielectric breakdown. These preferred voltages reflect, among other things, a preference for voltages that are readily driven in high-density arrangements with off-the-shelf electronics.

Preferably, over an operating period of time encompassing at least one polarity cycle either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_2$ carried by the current associated with the other polarity is between about 1:½ and about ½:1. The voltage-integrated areas are the voltage profiles integrated over the relevant time period. Preferably, the operation of the pump satisfies one of the ratio parameters when the pump is operated over a period of time of at least about 10 seconds without generating a sufficient rate of bubbling to stop liquid flow. More preferably, the first ratio or the second ratio is between about 1:0.8 and about 0.8 1, yet more preferably the first or second ratio is between about 1:0.9 and about 0.9:1, still more preferably is between about 1:0.95 and about 0.95:1, yet still more preferably is between about 1:0.98 and about 0.98:1. In a highly preferred embodiment, the apparatus is operated pursuant to a control mechanism set such that one of these ratios is equal to one. Of course, the limitations of the control mechanism will imply some operational variance from this control target, but in this latter embodiment the effective ratio should remain within about 20% of 1.

In one aspect of the first embodiment, the electrode-based pump comprises three or more electrodes, and wherein the voltage monitored at two of the electrodes displays the periodically reversing voltage.

Preferably, the pump is operated to pump at liquid with a time averaged pressure of P and with no gas nucleations observable by eye or by the aid of a microscope, and wherein the liquid that would, if the electrodes were driven by a constant DC voltage effective to pump the liquid with pressure P, generate gas nucleations that would be observable by eye. Preferably, the pump is operated to pump at liquid with no gas nucleations observable by eye, wherein the liquid has a conductivity of at least about $10^{-4}$ S/m. In another aspect of the invention, the pump can be operated without bubble generation with a liquid having a conductivity of at least about $10^{-3}$ S/m, or at least about $10^{-2}$ S/m.

In a second embodiment, the invention provides an apparatus for pumping liquid with an electrode-based pump having a liquid flow pathway, the apparatus comprising: a channel of capillary dimensions forming at least part of the flow pathway; a pump comprising at least two electrodes inserted into the flow pathway; a controller for controlling the voltages applied to the electrodes such that the pumps operate under a sequentially repeated pattern of polarity cycles, and such that over the period of the repeated pattern either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_2$ carried by the current associated with the other polarity is between about 1:½ and about ½:1. Preferably, the controller operates pursuant to a programmable microprocessor, and wherein the microprocessor is programmed to sequentially and repetitively operate the pattern of polarity cycles. Preferably, either (i) the electrodes are inserted into the channel or (ii) the flow pathway comprises a reservoir for feeding liquid to the channel, one or more electrodes of the pump are inserted into the reservoir, and one or more of the electrodes are inserted into the channel.

In a first aspect of a third embodiment, the invention provides a method of operating a capillary electrophoresis apparatus having at least one electrode at each end of an electrophoresis pathway and operating with an electrophoresis liquid, the method comprising: periodically reversing the voltage polarity applied to the electrodes while maintaining a net electrophoretic migration of one or more solutes in a desired direction. Preferably, the method further comprises selecting a pattern of polarity reversals and an associated voltage amplitude profile reduce or eliminate the nucleation of gas at the electrodes. Preferably, the voltage polarity reversals are applied by repeating a defined pattern with a defined frequency, wherein the defined pattern comprises a voltage amplitude profile of a first polarity, which first polarity causes electrophoresis of the one or more solutes in the desired direction, and a voltage amplitude profile of a second polarity opposite that of the first. Preferably, the frequency is at least about 10 Hz. Preferably, the frequency is from about 10 Hz to about 100 MHz, more preferably from about 100 Hz to about 10 kHz, yet more preferably from about 100 Hz to about 1 kHz.

As above, preferably the maximum voltage applied of the first polarity is greater than the maximum voltage applied of the second polarity. Preferably, the maximum voltage of the second polarity is no more than about 50% of the maximum voltage of the first polarity, more preferably no more than about 40%, yet more preferably no more than about 30%.

Preferably, over an operating period of time encompassing at least one polarity cycle either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_2$ carried by the current associated with the other polarity is between about 1:½ and about ½:1. Preferably, the operation of the electrodes satisfies one of the ratio parameters when the pump is operated over a period of time of at least about 10 seconds without generating a sufficient rate of bubbling to retard electrophoretic migration. Preferably, the first ratio or the second ratio is between about 1:0.8 and about 0.8:1, more preferably the first or second ratio is between about 1:0.9 and about 0.9:1, yet more preferably is between about 1:0.95 and about 0.95:1, yet still more preferably is between about 1:0.98 and about 0.98:1. In a highly preferred embodiment, the apparatus is operated pursuant to a control mechanism set such that one of these ratios is equal to one. Of course, the limitations of the control mechanism will imply some operational variance from this control target, but in this latter embodiment the effective ratio should remain within about 20% of 1.

Preferably, the electrodes are operated to move a the solute with a time averaged mobility of M and with no gas nucleations observable by eye, and wherein the liquid that would, if the electrodes were driven by a constant DC voltage effective to move the one solute with a mobility of M, generate gas nucleations that would be observable by eye. Preferably, the electrodes are operated to move one solute with no gas nucleations observable by eye, wherein the liquid has a conductivity of at least about $10^{-2}$ S/m.

In a second aspect of the third embodiment, the invention provides a method of operating an electrophoresis apparatus having at least one electrode at each end of an electrophoresis pathway and operating with an electrophoresis liquid, the method comprising periodically reversing the voltage polarity applied to the electrodes while maintaining a net electrophoretic migration of one or more solutes in a desired direction, wherein a pattern of polarity reversals and an associated voltage amplitude profile are selected to reduce or eliminate the nucleation of gas at the electrodes. Preferably, the voltage polarity reversals are applied by repeating a defined pattern with a defined frequency of at least about 10 Hz.

In a fourth embodiment of the invention, the invention provides an electrophoresis apparatus having at least one electrode at each end of an electrophoresis pathway comprising: two electrodes situated such that the distance between them encompasses the electrophoresis pathway, in which pathway electrophoretic separation is anticipated to occur; a controller for controlling the voltages applied to the electrodes such that the electrodes operate under a sequentially repeated pattern of polarity cycles, and such that over the period of the repeated pattern either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_2$ carried by the current associated with the other polarity is between about 1:½ and about ½:1. Preferably, the controller operates pursuant to a programmable microprocessor, and wherein the microprocessor is programmed to sequentially and repetitively operate the pattern of polarity cycles. In an embodiment, the apparatus incorporates for the electrophoresis pathway additional electrodes at one or both ends.

Definitions

The following terms shall have, for the purposes of this application, the meaning set forth below. In particular, for the purpose of interpreting the claims, the term definitions shall control over any assertion of a contrary meaning based on other text found herein:

Capillary Dimensions

"Capillary dimensions" are dimensions that favor capillary flow of a liquid. Typically, channels of capillary dimensions are no wider than about 1.5 mm. Preferably channels are no wider than about 500 µm, yet more preferably no wider than about 250 µm, still more preferably no wider than about 150 µm.

Polarity Cycle

A polarity cycle is the whole of (a) a continuous period operating with one of the polarities, and (b) an immediately following continuous period operating with the opposite polarity.

DETAILED DESCRIPTION OF THE INVENTION

Electrode-based Pumping

Figure 1:
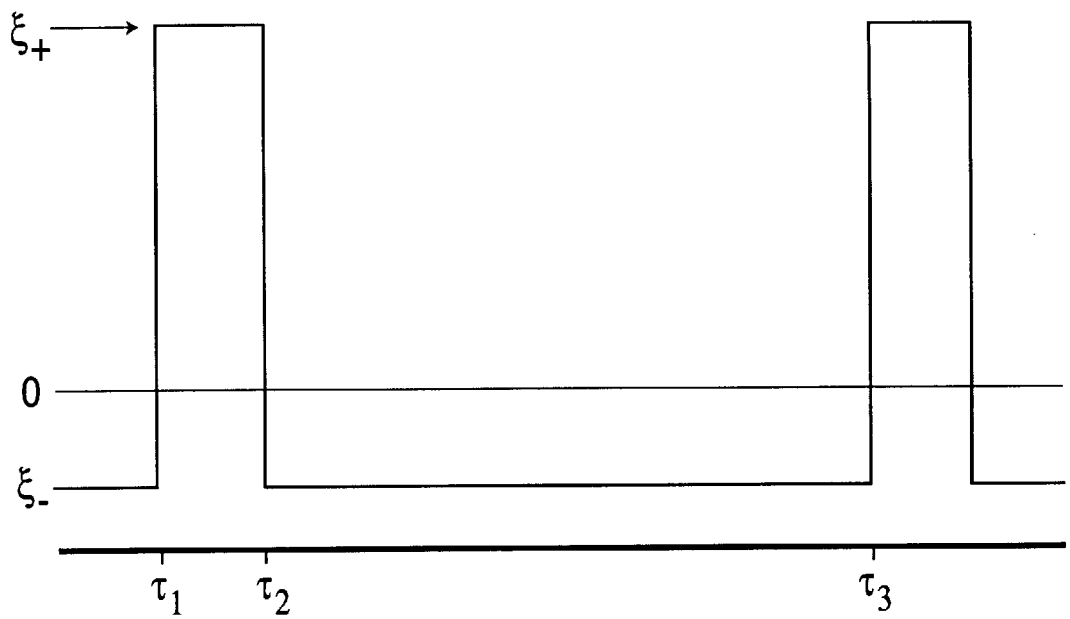
FIG. 1 displays a square wave voltage driving pattern.

The present invention had its origin in the observation that in electrode-based pumping processes, particularly in electrohydrodynamic pumping processes, a number of liquids exhibited excessive bubbling. These are typically liquids with relatively high conductivity such as 0.1 M butylamine in dimethylformamide (conductivity 0.007 S/m), but include other liquids of lower conductivity. It has now been observed that net fluid movement in the desired direction could be maintained while minimizing electrolysis, other electrochemical processes, or like bubble-generating events at the electrodes by periodically reversing the polarity applied to the electrodes. In perhaps its most simple form, the invention uses a repeat pattern of a square wave of voltage of a first polarity which drives pumping in the desired direction followed by a square wave of lower amplitude and longer duration, as illustrated in FIG. 1. The initial observation was that optimization of bubble minimization appeared to occur when the product of the amplitude of the first square wave times its duration was approximately equal to the corresponding product for the second square wave. In the generalized statement of this principle, one compares the areas defined by integrating voltage amplitude over time. Without being bound by theory, it is believed that these areas serve as a surrogate for the more important parameters, which are the net charges carried by the respective voltage polarities. However, this area measurement is generally the most readily measured parameter and, at least over the voltage ranges most useful for operating the electrode-based devices of the invention, is highly correlated with the net charge parameter. This correlation is due to the current, over the relevant voltage range, being substantially linearly related to the voltage.

In FIG. 1, a square wave of voltage of a polarity that causes the desired pumping is applied over a period of $t_+=(\tau_2-\tau_1)$ and has an amplitude of $\xi_+$. Immediately thereafter, an opposite polarity voltage of amplitude $\xi_-$ is applied for a period of $t_-=(\tau_3-\tau_2)$. $\xi_+$ is larger than $\xi_-$, such that $\xi_+=b\xi_-$, where b is larger than 1. $t_+$ is shorter than $t_-$, such that $(t_+)=c(t_-)$, where c is smaller than 1. These values are selected such that $(\xi_+)(t_+)=(\xi_-)(t_-)$.

Applicant believes that the theoretical basis for why net fluid movement occurs even when the net charges carried by the two opposing voltages are equal has been identified. This theory is presented below, though of course the invention is not restricted to the theory. With simple square wave voltage driving patterns, the experimental observation is that net liquid movement is dictated by the larger amplitude square wave. For more complex patterns, simple empirical examinations can identify the net direction of flow, or resort can be made to the guidance provided by the theory presented below. The theory implies that pumping pressure is related to the square of the voltage amplitude. Accordingly, the ratio of pressure generated in a driving portion of the voltage driving pattern to that generated in the reverse portion can be much greater than the ratio of the associated voltages, resulting in greater flow in the desired direction.

Without being bound by any particular theory, possible theoretical considerations in electrode-based pumping are set forth in detail in U.S. application Ser. No. 08/556,423, filed Nov. 9, 1995 (DSRC 11717A). At least two types of such electrode-based pumping, i.e., electrokinetic pumping, have been described, typically under the names "electrohydrodynamic pumping" (EHD) and "electroosmosis" (EO). EHD pumping has been described by Bart et al., "Microfabricated Electrohydrodynamic Pumps," *Sensors and Actuators*, A21–A23:193–197, 1990 and Richter et al., "A Micromachined Electrohydrodynamic Pump," *Sensors and Actuators*, A29:159–168, 1991. EO pumps have been described by Dasgupta et al., "Electroosmosis: A Reliable Fluid Propulsion System for Flow Injection Analysis," *Anal. Chem.*, 66:1792–1798, 1994.

EO pumping is believed to take advantage of the principle that the surfaces of many solids, including quartz, glass and the like, become charged, negatively or positively, in the presence of ionic materials, such as salts, acids or bases. The charged surfaces will attract oppositely charged counter ions in solutions of suitable conductivity. The application of a voltage to such a solution results in a migration of the counter ions to the oppositely charged electrode, and moves the bulk of the fluid as well. The volume flow rate is proportional to the current, and the volume flow generated in the fluid is also proportional to the applied voltage. Typically, in channels of capillary dimensions, the electrodes that cause flow can be spaced further apart than in EHD pumping, since the electrodes are only involved in applying force, and not, as appears to apply in EHD, in creating charges on which the force will act. EO pumping is generally perceived as a method appropriate for pumping conductive solutions.

The present invention is believed to be applicable to all forms of electrode-based pumping, which pumping is also referred to herein as "electrokinetic" pumping. The invention is most preferably applied to electrode-based pumping where the field strength directly acts on liquid components to create pressure, as in EHD and EO. The invention is also applicable to other electrode-based methods, such as traveling wave methods, that are believed to operate by creating heat convection forces.

The pumps applied in the present invention can be made of simple wire electrodes. Alternatively, where high density arrangements of electrode-based pumps are anticipated, reference can be made to U.S. application Ser. No. 08/554,887, filed Nov. 9, 1995 (DSRC 11948), which describes methods of mass producing high density microelectrodes using microfabrication techniques. This application is hereby incorporated into this disclosure by reference in its entirety. These electrodes are formed on plates of dielectric material such as glass, and each such plate is bonded to a plate in which channels have been etched. See U.S. Application Ser. No. 08/745,766, filed Nov. 8, 1996 (DSRC 11865A) for plate bonding methodology, which application is hereby incorporated into this disclosure by reference in its entirety.

References are made herein to pumping (or electrophoresis) parameters that minimize the gas nucleations observable by eye. It should be recognized that, in circumstances where the electrodes cannot be viewed directly, this reference is to conditions which, if repeated in a comparable device where the electrodes can be viewed, shows an appropriate level of gas nucleations.

It should be recognized that the invention can be applied in several contexts beyond simple two-electrode pumps, and that these contexts are intended to be within the scope of the claims. For example, the invention can be applied where several electrodes are incorporated into a channel to allow flexibility in selecting electrodes most appropriate for pumping a particular fluid. In complex electrode-based pumping protocols, such as traveling wave protocols, the invention is being utilized if it is used with respect to the voltage patterns applied to two electrodes in the array of electrodes.

Theoretical Considerations

Without being limited to theory, it is believed that the following conditions have to be satisfied in order to have a net fluid flow in one direction without gas nucleation in the electrodes:

A1) Symmetry condition $$\int_{\tau_1}^{\tau_3} v(t)dt \approx 0 \tag{1}$$

The values $\tau_1, \tau_2$ and $\tau_3$ designate, respectively, the start time of a polarity cycle, the end time for the first continuous period operating under a first polarity, and the end time for the following continuous period operating under the second polarity, as illustrated in FIG. 1. This condition indicates that the area of the positive part $A_1$ of the voltage waveform is approximately equal to the area of the negative part $A_2$ of the voltage waveform. This condition can be expressed as $$A_1 = \int_{\tau_1}^{\tau_2} v(t)dt \tag{2}$$

$$A_2 = \int_{\tau_2}^{\tau_1} v(t)dt$$

$A_1 \approx A_2$

A2) Asymmetry condition:

$\xi_+ > \xi_-$, where $\xi_+$ and $\xi_-$ are, respectively, applied voltages during the first continuous period of the polarity cycle and the second continuous period. This condition indicates that in order to obtain a net fluid flow the amplitude of the positive part of the voltage waveform has to be larger than the amplitude of the negative part of the voltage waveform Experimental results suggest that, in preferred operations of the pumps, a balance of charges exists during positive and negative pulses. Consider a pulse as shown in FIG. 1, where $\xi_+$ is the positive amplitude, $\xi_-$ is the negative amplitude, $t_+(=\tau_2-\tau_1)$ is the duration of the positive pulse, and $t_-(=\tau_3-\tau_2)$ is the duration of the negative pulse. Considering a resistive system, the charge during the positive pulse $q_1$ and the charge during the negative pulse $q_2$ can be written as $$q_1 = \int_{\tau_1}^{\tau_2} i(t)dt \tag{3}$$

and $$q_2 = \int_{\tau_2}^{\tau_3} i(t)dt \tag{4}$$

where i(t) is the current as a function of time. The experimental observation suggests that the bubble formation or gas nucleation at the electrodes is minimized and in many cases eliminated when the charge in the positive pulse is comparable to the charge in the negative pulse.

$$q_1 \approx q_2 \tag{5}$$

For a square pulse excitation like FIG. 1 and for a resistive system, the charge balance condition gives the following expression $$\xi_+ t_+ = \xi_- t_- \tag{6}$$

Assuming that the positive voltage amplitude is b times the negative voltage amplitude and that the positive voltage duration is c times the negative voltage duration.

$\xi_+ = b\xi_-$ $$t_+ = ct_- \tag{7}$$

Then, we have to satisfy the following condition $$bc=1 \tag{8}$$

B) Net fluid flow:

Experimental observations indicate that a net fluid flow is obtained. From the theoretical point of view, the following seeks to determine the relationship between the mass transferred during the positive and negative pulses. According to Stuetzer (W. F. Pickard, *J. Appl. Phys.*, 34:246, 1963), the pressure developed by ion drag pumping like EHD pumping is given by:

$$P = \frac{9}{8}\varepsilon E_0^2 \langle \eta \rangle \tag{9}$$

where $$E_o = -\frac{V}{l} \tag{10}$$

where l is the distance between electrodes, V is the potential and $\langle \eta \rangle$ is a dimensionless parameter. Therefore, the pressures generated by the positive and negative pulses are given by $$P_+ = \langle a \rangle \frac{\xi_+^2}{l^2} \quad (11)$$

$$P_- = \langle a \rangle \frac{\xi_-^2}{l^2}$$

The pressure P is given by $$P = RQ \quad (12)$$

where $$Q = \frac{Vol}{t} \quad (13)$$

R is the fluid flow resistance, Q is the fluid flow, Vol is the volume and t is the time using equations (11) and (12), we can write $$\frac{\xi_+^2}{\xi_-^2} = \frac{Q_+}{Q_-} \quad (14)$$

Using equations (13), (14) and (7), we obtain $$Vol_+ = b^2 Vol_- \quad (15)$$

Where $Vol_+$ is the volume displaced during the positive cycle in one direction and $Vol_-$ is the volume displaced during the negative circle in the opposite direction. Multiplying both sides by the density (fluid density, $d = m_+/Vol_+ = m_-/Vol_-$, where $m_+$ and $m_-$ are the masses of the volumes moved by the electrode-based pumps), we obtain:

$$m_+ = b^2 c m_- \quad (16)$$

Applying the energy condition $bc = 1$, we have:

$$m_+ = b m_- \quad (17)$$

Thus, if $b \neq 1$, meaning that the two voltage amplitudes are asymmetric, there will be a net mass transfer of fluid.

Electrophoresis

The same types of operational guidelines as apply for electrode-based pumping apply for electrophoresis. The major difference is that when seeking to electrophores a certain class of molecules voltage parameters will be selected based on the voltages typically used, in contexts outside of the present invention, with comparable electrophoresis devices, and these voltages may not be similar to the voltages used with like fluids in the electrode-based pumping context.

Drivers

Figure 2:
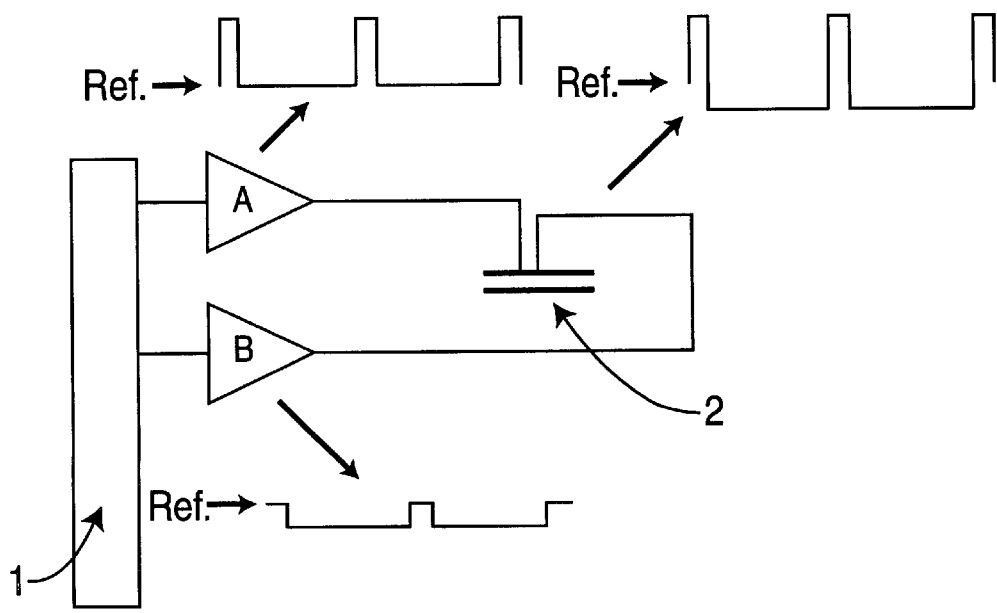
FIG. 2 shows a schematic of electrical drivers that can be used with the invention.

Driving circuits are set forth in U.S. application Ser. No. 08/469,238, filed Jun. 6, 1995 (DSRC 11717) and U.S. application Ser. No. 08/556,423, filed Nov. 9, 1995 (DSRC 11717A), which applications are incorporated herein in their entirety. A preferred circuit is set forth in FIG. 2. Box 1 houses control electronics, which can be interfaced with a computer. Solid state switch A (for example a transistor or an operational amplifier) is used to generate a positive cycle (or if the driving polarity is negative, a negative cycle). Solid state switch B is used to generate a negative cycle (or if the driving polarity is negative, a positive cycle). The voltage applied to the pump 2 is a combination of the two waveforms. The waveforms generated by two illustrated switches A and B, and the resulting waveform, are represented in the figure, with an indication of a reference voltage.

Microfluidics Devices

United States patent application No. 08/556,036, filed May 31, 1995 (DSRC 11402G), No. 08/483,331, filed Jun. 7, 1995 (DSRC 11740), No. 08/730,636, filed Oct. 11, 1996 (DSRC 12385), and No. 08/744,386, Nov. 7, 1996 (DSRC 12385A) describe liquid distribution systems. Typically, these systems form, in sandwiched layers of a substrate which is preferably glass, reservoirs and connected complex networks of channels. The liquids in the reservoirs are typically maintained feeds from external containers. By selectively activating electrode-based pumps, liquids from a reservoir can be selectively distributed to reaction cells via the channels. Often, the electrodes are inserted into the channels. In some embodiments, however, particularly where a reservoir contains liquids of relatively high conductivity, one or more of the driving electrodes can be placed in the reservoir so as to provide the relatively greater spacing between the driving electrodes that favors the EO mechanism of electrode-based pumping. Typically, where a reservoir has such electrodes, the electrode-based pumps that selectively drive liquid through the channels each will include a separate set of one or more electrodes inserted into each channel connected to the reservoir, but a plurality of such pumps will share electrodes located in the connected reservoir.

The following examples further illustrate the present invention, but of course, should not be construed as in any way limiting its scope.

EXAMPLE

For the example, a planar pump in a channel 240 $\mu$m wide and 80 $\mu$m deep was used. The pump was two electrodes inserted into the channel with a 250 $\mu$m spacing between them.

1) A 0.1 M solution of butylamine in dimethylformamide was pumped under DC conditions and separately pursuant to the invention. The DC conditions were the application of 40 V, which resulted in immediate bubbling. Pumping stopped as a result of the bubbling. Two sets of conditions pursuant to the invention were applied as follows:

|   | Frequency | Voltages | Periods |
|---|---|---|---|
| A | 1 kHz | $\xi_+ = 500$ V<br>$\xi_- = -125$ V | $\tau_+ = 0.2$<br>$\tau_- = 0.8$ |
| B | 500 Hz | $\xi_+ = 500$ V<br>$\xi_- = -125$ V | $\tau_+ = 0.4$<br>$\tau_- = 0.6$ |

Under both conditions A and B, fluid flow is generated by the pump without gas nucleation or bubbling.

2) Dimethylformamide, containing a trace of water, was pumped under DC conditions and separately pursuant to the invention. The DC conditions were the application of 40 V, which resulted in bubbling at both electrodes. Conditions pursuant to the invention were applied as follows:

|   | Frequency | Voltages | Periods |
|---|---|---|---|
| C | 1 kHz | $\xi_+ = 300$ V<br>$\xi_- = -75$ V | $\tau_+ = 0.2$ ms<br>$\tau_- = 0.8$ ms |

Conditions C avoided the formation of bubbles.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of operating an electrode-based pump to pump a liquid, the method comprising
periodically reversing the voltage polarity applied to the electrodes of the pump with a frequency of at least 10 Hz while maintaining a net flow of liquid in a desired direction.

2. The method of claim 1, further comprising selecting a pattern of polarity reversals and an associated voltage amplitude profile to reduce or eliminate the nucleation of gas at the electrodes.

3. The method of claim 1, wherein the voltage polarity reversals are applied by repeating a defined pattern, wherein the defined pattern comprises a voltage amplitude profile of a first polarity, which first polarity causes pumping in the desired direction, and a voltage amplitude of a second polarity opposite that of the first.

4. The method of claim 1, wherein the maximum voltage applied of the first polarity is greater than the maximum voltage applied of the second polarity.

5. The method of claim 1, wherein over an operating period of time encompassing at least one polarity cycle either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_2$ carried by the current associated with the other polarity is less than 1:½ and more than about ½:1.

6. The method of claim 5, wherein the operation of the pump satisfies one of said ratio parameters when the pump is operated over a period of time of at least about 10 seconds without generating a sufficient rate of bubbling to stop liquid flow.

7. The method of claim 5, wherein the first ratio or the second ratio is between about 1:0.8 and about 0.8:1.

8. The method of claim 1, wherein the electrode-based pump comprises three or more electrodes, and wherein the voltage monitored at two of the electrodes displays said periodically reversing voltage.

9. The method of claim 1, wherein the pump is operated to pump a liquid with a time averaged pressure of P and with no gas nucleations observable by the aid of a microscope, and wherein the liquid that would, if the electrodes were driven by a constant DC voltage effective to pump the liquid with pressure P, generate gas nucleations that would be observable by eye.

10. The method of claim 1, wherein the pump is operated to pump a liquid with no gas nucleations observable by eye, wherein the liquid has a conductivity of at least about $10^{-4}$ S/m.

11. The method of claim 1, wherein the frequency is from 100 Hz to 100 MHz.

12. The method of claim 1, wherein the frequency is from about 100 Hz to about 10,000 Hz.

13. The method of claim 1, wherein the frequency is from about 100 Hz to about 1,000 Hz.

14. An apparatus for pumping liquid with an electrode-based pump having a liquid flow pathway, the apparatus comprising:
a channel of capillary dimensions forming at least part of the flow pathway;
a pump comprising at least two electrodes inserted into the flow pathway;
a controller for controlling the voltages applied to the electrodes such that the pumps operate under a sequentially repeated pattern of polarity cycles, and such that over the period of the repeated pattern either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_1$ carried by the current associated with the other polarity is less than 1:½ and more than about ½:1.

15. The apparatus of claim 14, wherein the controller operates pursuant to a programmable microprocessor, and wherein the microprocessor is programmed to sequentially and repetitively operate said pattern of polarity cycles.

16. The apparatus of claim 14, wherein either
(i) the electrodes are inserted into the channel or
(ii) the flow pathway comprises a reservoir for feeding liquid to the channel, one or more electrodes of the pump are inserted into the reservoir, and one or more of the electrodes are inserted into the channel.

17. A method of operating a capillary electrophoresis apparatus having at least one electrode at each end of an electrophoresis pathway and operating with an electrophoresis liquid, the method comprising
periodically reversing the voltage polarity applied to the electrodes while maintaining a net electrophoretic migration of one or more solutes in a desired direction; wherein the periodic reversal of the voltage polarity comprises a pattern of polarity reversals and an associated voltage amplitude profile selected to reduce or eliminate the nucleation of gas at the electrodes, wherein the frequency of the polarity cycle is at least 100 Hz.

18. The method of claim 17, wherein the voltage polarity reversals are applied by repeating a defined pattern with a defined frequency, wherein the defined pattern comprises a voltage amplitude profile of a first polarity, which first polarity causes electrophoresis of the one or more solutes in the desired direction, and a voltage amplitude profile of a second polarity opposite that of the first.

19. The method of claim 18, wherein over an operating period of time encompassing at least one polarity cycle either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_2$ carried by the current associated with the other polarity is between about 1:½ and about ½.

20. The method of claim 19, wherein the operation of the electrodes satisfies one of said ratio parameters when the electrodes are operated over a period of time of at least about 10 seconds without generating a sufficient rate of bubbling to retard electrophoretic migration.

21. The method of claim 19, wherein the first ratio or the second ratio is between about 1:0.9 and about 0.9:1.

22. The method of claim 17, wherein the electrodes are operated to move one said solute with a time averaged mobility of M and with no gas nucleations observable by eye, and wherein the liquid would, if the electrodes were driven by a constant DC voltage effective to move said one solute with a mobility of M, generate gas nucleations that would be observable by eye.

23. The method of claim 17, wherein the electrodes are operated to move one said solute with no gas nucleations observable by eye, wherein the liquid has a conductivity of at least about $10^{-4}$ S/m.

24. A method of operating an electrophoresis apparatus having at least one electrode at each end of an electrophoresis pathway and operating with an electrophoresis liquid, wherein the electrodes are enclosed within a microfluidic device such that nucleations of gas at the electrodes interfere with current flow between the two electrodes, the method comprising periodically reversing the voltage polarity applied to the electrodes while maintaining a net electrophoretic migration of one or more solutes in a desired direction, wherein a pattern of polarity reversals and an associated voltage amplitude profile are selected to reduce or eliminate the nucleation of gas at the electrodes, and wherein the voltage polarity reversals are applied by repeating a defined pattern with a frequency of at least 100 Hz.

25. An electrophoresis apparatus having at least one driving electrode at each end of an electrophoresis pathway comprising:

two driving electrodes situated such that the distance between them encompasses the electrophoretic pathway, in which pathway electrophoretic separation is anticipated to occur;

additional driving electrodes at one or both ends of the electrophoretic pathway; and, a controller for controlling the voltages applied to the electrodes such that the electrodes operate under a sequentially repeated pattern of polarity cycles, and such that over the period of the repeated pattern either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_2$ carried by the current associated with the other polarity is between about 1:½ and about ½:1, and wherein the maximum voltage applied of the first polarity, which first polarity causes electrophoresis in the desired direction of one or more solutes in an electrophoresis liquid, is greater than the maximum voltage applied of the second polarity.

26. The apparatus of claim 25, wherein the controller operates pursuant to a programmable microprocessor, and wherein the microprocessor is programmed to sequentially and repetitively operate said pattern of polarity cycles.

27. A method of operating an electrode-based pump to pump a liquid, the method comprising periodically reversing the voltage polarity applied to the electrodes of the pump while maintaining a net flow of liquid in a desired direction; wherein over an operating period of time encompassing at least one polarity cycle either (a) a first ratio of a voltage-integrated area A1 associated with a first polarity to a voltage-integrated area associated with the other polarity or (b) a second ratio of a charge q1 carried by the current associated with a first polarity to a charge q2 carried by the current associated with the other polarity is less than 1:½ and more than about ½:1.

28. The method of claim 27, further comprising selecting a pattern of polarity reversals and an associated voltage amplitude profile to reduce or eliminate the nucleation of gas at the electrodes.

29. The method of claim 27, wherein the frequency is at least 100 Hz.

30. The method of claim 27, wherein the first ratio or the second ratio is between about 1:0.9 and about 0.9:1.

31. A method of operating a liquid distribution system comprising, in a substrate, channels of capillary dimensions for conveying liquids and, for moving the liquids, one or more electrode-based pumps each such pump comprising electrodes in electrical contact with one of said channels, the method comprising periodically reversing the voltage polarity applied to the electrodes of a given said pump while maintaining a net flow of liquid in a desired direction in the corresponding channel, wherein the voltage polarity cycles are applied by repeating a defined pattern with a defined frequency of at 10 Hz.

32. The method of claim 31, wherein the voltage polarity cycles are applied by repeating a defined pattern with a defined frequency of at least 100 Hz, and wherein the maximum voltage applied of the first polarity is greater than the maximum voltage applied of the second polarity.

33. The method of claim 31, wherein over an operating period of time encompassing at least one polarity cycle either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_2$ carried by the current associated with the other polarity is less than 1:½ and more than about ½:1.

34. The method of claim 33, wherein the first ratio or the second ratio is between about 1:0.9 and about 0.9:1.

35. The method of claim 31, wherein the pump is operated to pump a liquid with a time averaged pressure of P and with no gas nucleations observable by eye, and wherein the liquid would, if the electrodes were driven by a constant DC voltage effective to pump the liquid with pressure P, generate gas nucleations that would be observable by eye.

* * * * *